(12) United States Patent
Carpenter et al.

(10) Patent No.: US 10,420,892 B2
(45) Date of Patent: Sep. 24, 2019

(54) DRIVE MECHANISM FOR A MEDICAMENT DELIVERY DEVICE

(71) Applicant: CAREBAY EUROPE LTD, Sliema (MT)

(72) Inventors: Lucas Carpenter, New Taipei (TW); Stephan Mueller, Taoyan (TW)

(73) Assignee: SHL MEDICAL AG, Zug (CH)

( * ) Notice: Subject to any disclaimer, the term of this patent is extended or adjusted under 35 U.S.C. 154(b) by 18 days.

(21) Appl. No.: 15/518,578

(22) PCT Filed: Oct. 1, 2015

(86) PCT No.: PCT/EP2015/072689
§ 371 (c)(1),
(2) Date: Apr. 12, 2017

(87) PCT Pub. No.: WO2016/062517
PCT Pub. Date: Apr. 28, 2016

(65) Prior Publication Data
US 2017/0312440 A1    Nov. 2, 2017

(30) Foreign Application Priority Data

Oct. 22, 2014  (SE) ..................................... 1451257

(51) Int. Cl.
*A61M 5/315* (2006.01)
*A61M 5/20* (2006.01)
*A61M 5/32* (2006.01)

(52) U.S. Cl.
CPC ...... *A61M 5/31511* (2013.01); *A61M 5/2053* (2013.01); *A61M 5/2033* (2013.01);
(Continued)

(58) Field of Classification Search
CPC .......... A61M 5/31511; A61M 5/31513; A61M 5/2053; A61M 5/415; A61M 5/14526
See application file for complete search history.

(56) References Cited

U.S. PATENT DOCUMENTS 3,343,539 A * 9/1967 Moorhouse .......... A61D 19/027
141/27
4,093,108 A * 6/1978 Hein .................. A61M 5/31511
222/401
(Continued)

FOREIGN PATENT DOCUMENTS

| EP | 1349590 B1 | 5/2006 |
|---|---|---|
| WO | 01/45772 A1 | 6/2001 |
| WO | 2004/011065 A1 | 2/2004 |

OTHER PUBLICATIONS

International Search Report and Written Opinion for Int. App. No. PCT/EP2015/072689, dated Dec. 22, 2015.

*Primary Examiner* — Shefali D Patel
(74) *Attorney, Agent, or Firm* — McDonnell Boehnen Hulbert & Berghoff LLP

(57) ABSTRACT

The present disclosure relates to a drive mechanism for a medicament delivery device according to the disclosure comprises a compression member comprising a first cavity containing a first volume of fluid, said compression member also comprising a second cavity containing a second volume of fluid; a passage for fluid communication between the first cavity and the second cavity; a first movable piston arranged to seal the first cavity; a second movable piston arranged to seal the second cavity; wherein movement of the first movable piston or of the second movable piston, by an applied force, causes a relative change of volume between the first volume of fluid and the second volume of fluid, via a fluid flow through said passage, such that the respective second movable piston or the first movable piston is also moved.

18 Claims, 14 Drawing Sheets

(52) U.S. Cl.
CPC ......... *A61M 5/3204* (2013.01); *A61M 5/3272* (2013.01); *A61M 2005/206* (2013.01); *A61M 2005/2013* (2013.01); *A61M 2005/3267* (2013.01)

(56) References Cited

U.S. PATENT DOCUMENTS 4,685,910 A * 8/1987 Schweizer ......... A61M 5/31511
604/218
6,171,276 B1 1/2001 Lippe et al.

* cited by examiner

DRIVE MECHANISM FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2015/072689 filed Oct. 1, 2015, which claims priority to Swedish Patent Application No. 1451257-8 filed Oct. 22, 2014. The entire disclosure contents of these applications are herewith incorporated by reference into the present application.

TECHNICAL FIELD

The present disclosure relates to a drive mechanism for a medicament delivery device and in particular to an improved, more user-friendly, automatic medicament delivery device providing a predetermined pressure when the medicament dose is to be delivered.

BACKGROUND

Many medicament delivery devices are developed for self-administration, i.e. a user performs the medicament delivery her-, or himself. This requires a medicament delivery device which is as safe to use and as easy to handle as possible. In order to meet these requirements, the risk of human errors must be minimized, the number of actions needed to be performed in order to receive a dose need to be reduced and the device must be intuitive and ergonomic to use. Thus, in order to minimize the risk of human errors, it is desirable to have the device as pre-assembled as possible.

Document EP 1349590 B describes an injector having a number of features that facilitate the handling of the injector. The penetration and injection is performed manually by simply pressing the proximal end of a needle shield against the delivery area, causing the shield to move in a distal direction, enabling the needle to penetrate the injection area and thereafter initialize the injection process. When the injection has been completed the injector is withdrawn whereby a needle shield extracts around the needle in a locked way.

Other aspects of injectors are the human aspect of handling the injector regarding how it is held during operation. A general aim is to have the patient holding the injector in an ergonomic way that permits penetration and injection in different locations on the body, such as around the waist and also on the backside of the waist and/or in the buttocks of the patient. Sometimes the patient or the injector do not reach the necessary pressure on the injector, as a result, the administered dose might be inaccurate causing undesired alterations on the patient.

It is considered important for the patient to receive the right dose after the injection has been made, in particular in instances when an injector is used where the patient does not see the injector, e.g. such as around the waist and also on the backside of the waist and/or in the buttocks of the patient.

Additionally, there is a need to simplify the drive mechanism of the medicament delivery device. New ways of creating propelling forces within the device are required in order to assure significant improvements on the weight and handling of the device. Moreover, the disclosure leads to important material savings for the producer, e.g. avoiding the use of several power springs.

SUMMARY

The object of the present disclosure is to provide a drive mechanism for a medicament delivery device with a propulsive force, which causes a controlled movement of a movable piston. The drive mechanism is configured to act on a medicament container for expelling a medicament.

The drive mechanism for a medicament delivery device according to the disclosure comprises a compression member comprising a first cavity containing a first volume of fluid, said compression member also comprising a second cavity containing a second volume of fluid; a passage for fluid communication between the first cavity and the second cavity; a first movable piston arranged to seal the first cavity; a second movable piston arranged to seal the second cavity; wherein movement of the first movable piston or of the second movable piston, by an applied force, causes a relative change of volume between the first volume of fluid and the second volume of fluid, via a fluid flow through said passage, such that the respective second movable piston or the first movable piston is also moved.

When a piston is moved, a volume of fluid flows between the first and the second cavity through the passage, creating a propulsive force which causes a controlled movement of the other movable piston.

According to another aspect of the disclosure, the first movable piston is longitudinally movable between a first position and a second position relative to the compression member and wherein the second movable piston is movable between a third and a fourth position relative to the compression member. Both the first and the second movable pistons are longitudinally movable, preferably slidable, in relation to the compression member.

According to yet another aspect of the disclosure, the first volume of fluid is larger than the second volume of fluid when the first movable piston is in the first position and the second movable piston is in the third position. Due to the relative change of volume between the first volume of fluid and the second volume of fluid, via the fluid flow through the passage, the second volume of fluid is larger than the first volume of fluid when the first movable piston is in the second position and the second movable piston is in the fourth position.

According to a further aspect of the disclosure, the drive mechanism further a distal tubular housing in which the compression member is coaxially arranged and rotationally locked, and a connector member connected to the proximal end of the distal tubular housing for preventing a longitudinal and proximal displacement of the compression member. It is also considerable that the distal tubular housing and the connector member are integrally i.e. manufactured as one component.

According to yet a further aspect of the disclosure, the drive mechanism further comprises a force member configured to exert the force on the first movable piston. The force member is preferably arranged between a connector member and the first movable piston. Further, the force member may be a compression spring but it is also possible to use another type of force members known in the art.

According to another aspect of the disclosure, the drive mechanism further comprises an activator member configured to releasably hold said first movable piston in the first position when said first movable piston is under a bias of said force member. The activator member is movable, preferably rotatably arranged in relation to the first movable piston. It is possible that different types of releasable holding means or elements, known in the art, can be used and should not be limited those described in the detailed description.

According to yet another aspect of the disclosure, the first movable piston is released by a displacement of the activator member in relation to first movable piston.

According to a further aspect of the disclosure, the compression member comprises a distal plate having an outer tubular sleeve and an inner tubular sleeve and wherein the first cavity is defined by the space between the inner surface of the outer tubular sleeve, the distal plate and the outer surface of the inner tubular sleeve, and wherein the second cavity is defined by the inner surface of the inner tubular sleeve and the distal plate.

According to a further aspect of the disclosure, the drive mechanism further comprises a first seal which is positioned between a distal tubular housing and the compression member, creating a sealed space between the tubular housing and the compression member such that the space is sealed from ambient air pressure. The first seal is preferably a gasket.

According to another aspect of the disclosure, the passage is defined by a first part comprising a through-hole in the distal plate wherein said through-hole communicates to the first cavity, a second part comprising a channel between the compression member and the distal tubular housing through the sealed space, and a third part comprising a through-hole in the distal plate wherein said through-hole communicates with the second cavity such that the first cavity is in fluid communication with the second cavity through the first part, the second part and the third part.

According to another aspect of the disclosure, in an alternative embodiment, the passage is defined by a through-hole located at the distal end of the inner tubular sleeve.

It is also yet a further aspect of the disclosure, that a medicament delivery device comprises a drive mechanism according to the above disclosed features.

The medicament delivery device further comprises a medicament delivery member cover configured to force the activator member to move in relation to the first movable piston, when the medicament delivery member cover is pressed against a delivery site, for causing a rotational movement of the activator member in relation to the medicament delivery member cover.

Additionally, the medicament delivery device may be an automatic delivery device as an injector, an inhaler, a spray delivery device or the like.

As mentioned above, in automatic medicament delivery devices it is crucial for the patient to be completely certain that the administered dose corresponds to the prefilled dose on the medical device. This is accomplished by the drive mechanism of the disclosure, since a predetermined volume of fluid flowing through the passage corresponds to the propulsive force needed to control the movement of the second movable piston. Therefore, a regulated movement of the second movable piston leads to a precise volume, assuring the quantity of the dose to be expelled from the medicament container.

The medicament delivery device according to the present disclosure presents a number of advantages. There is a high degree of functionality and automation, which remove unnecessary components and actions for delivering a medicament.

Moreover, the present disclosure drive mechanism improves the weight issue and the proper handling of the device. Additionally, the disclosure leads to important material savings for the manufacturing processes avoiding the use of several power springs.

These and other aspects of and advantages with the present disclosure will become apparent from the following detailed description and from the accompanying drawings.

BRIEF DESCRIPTION OF THE DRAWINGS

In the following detailed description of the disclosure, reference will be made to the accompanying drawings, of which

DETAILED DESCRIPTION

In the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

Figure 1:
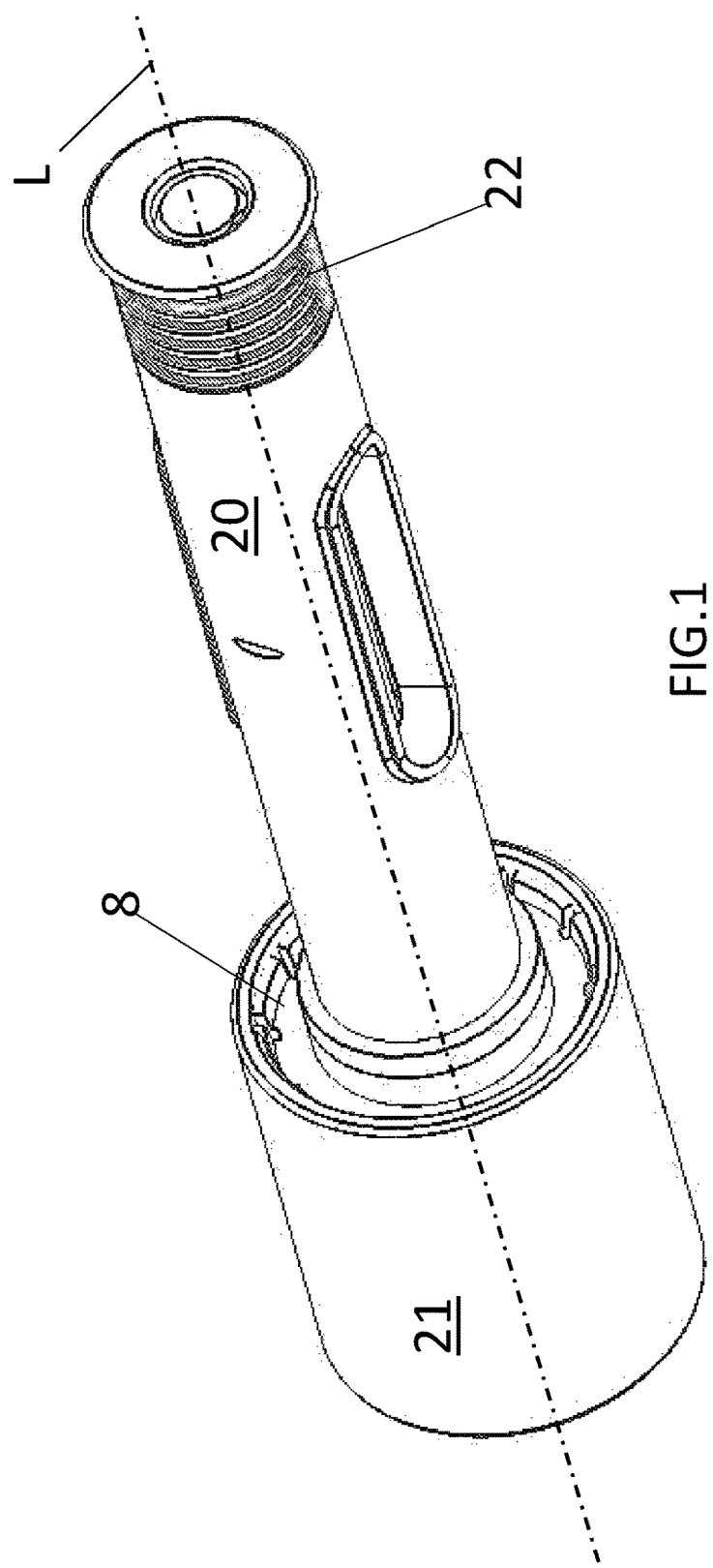
FIG. 1 shows a perspective view of different components of a medicament delivery device.

FIG. 1 shows a non-limiting example of a medicament delivery device where the present disclosure could be utilized. The medicament delivery device comprises a distal tubular housing 21 and a proximal tubular housing 20 connectable to each other by positive or non-positive connection means, more particularly by a connector member 8. The distal and proximal housings extend along a longitudinal extending axis L. A cap 22 may be removably attached to a proximal end of the proximal tubular housing 20. The delivery device is designed to be held in one hand for the delivery of a medicament.

Figure 2:
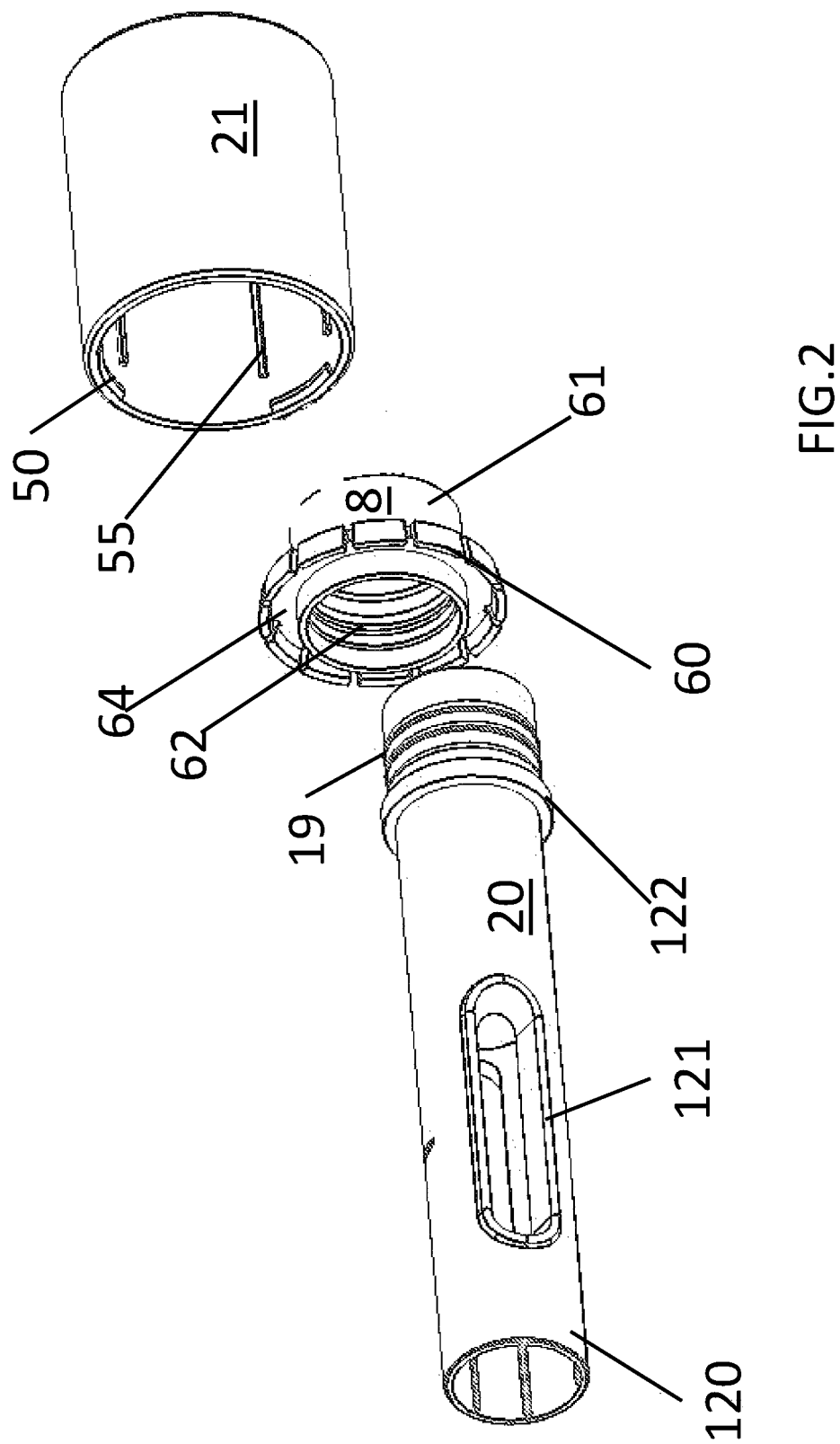
FIG. 2 shows an enlarged and exploded fragmented perspective view of the assembly of external tubular parts and a connector member.

FIG. 2 shows in more detail that the distal end of the proximal tubular housing 20 comprises an outer connection means 19 suitable to be connected to an inner connection means 62 of the connector member 8, preventing any relative movement of the housings 20, 21 in relation to each other. Further, the proximal tubular housing 20 comprises a proximal part 120, at least one opening 121, such as a window, for viewing the contents of the proximal housing 20. The proximal housing also comprises an annular protrusion 122 configured to abut the connector member 8 when the proximal tubular housing 20 is connected to the connector member 8. The distal tubular housing 21 comprises on its inner surface longitudinally extending ribs 55 and radially inwardly extending ledges 50. The radially inwardly extending ledges 50 are arranged near the proximal rim of the distal tubular housing 21. The connector cap 8 also comprises an inner tubular sleeve 61 which has a radially outwardly extending ledge 64. The radially outwardly extending ledge 64 comprises at its outer end a flange with equidistant resilient tongues 60. The inner connection means 62 is arranged on the inner surface of the inner tubular sleeve 61 of the connector member 8.

For assembly purposes the connector member 8 and the distal tubular housing are separate components but they can also be manufactured together as one component.

Figure 3:
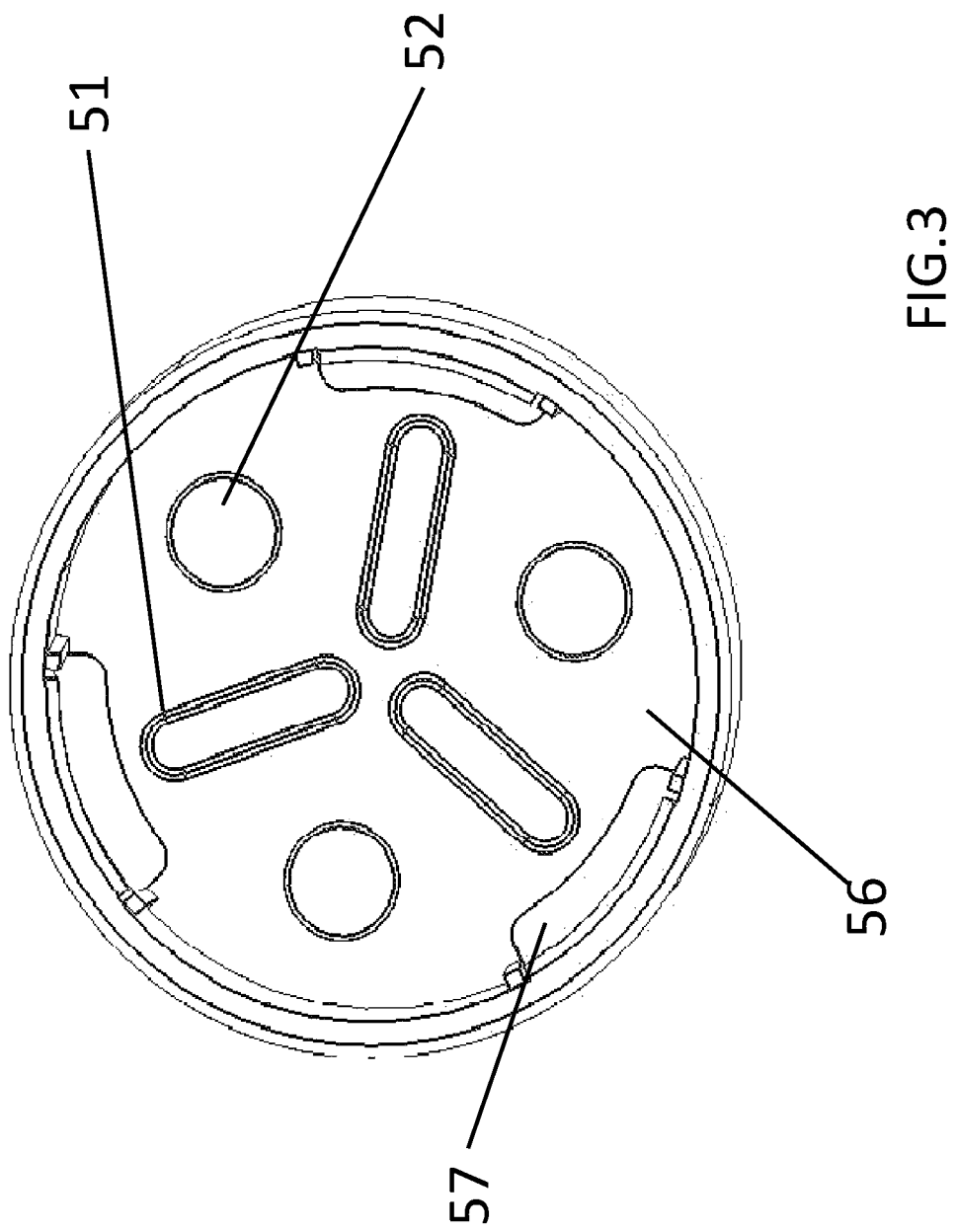
FIG. 3 illustrates an enlarged front elevation view seen from its proximal end of a distal tubular housing.

FIG. 3 shows the distal tubular housing 21 seen from its proximal end. The tubular distal housing further comprises a distal transversal wall 56. The distal transversal wall 56 comprises equidistant and elongated curved through holes 57 arranged near the inner surface of the tubular housing part 21, equidistant proximally extending protrusions 52 and equidistant elongated depressions 51, more specifically having an elliptical or oval shape. The equidistant proximally extending protrusions 52 and the equidistant elongated depressions 51 are alternately arranged in relation to each other.

Figure 4:
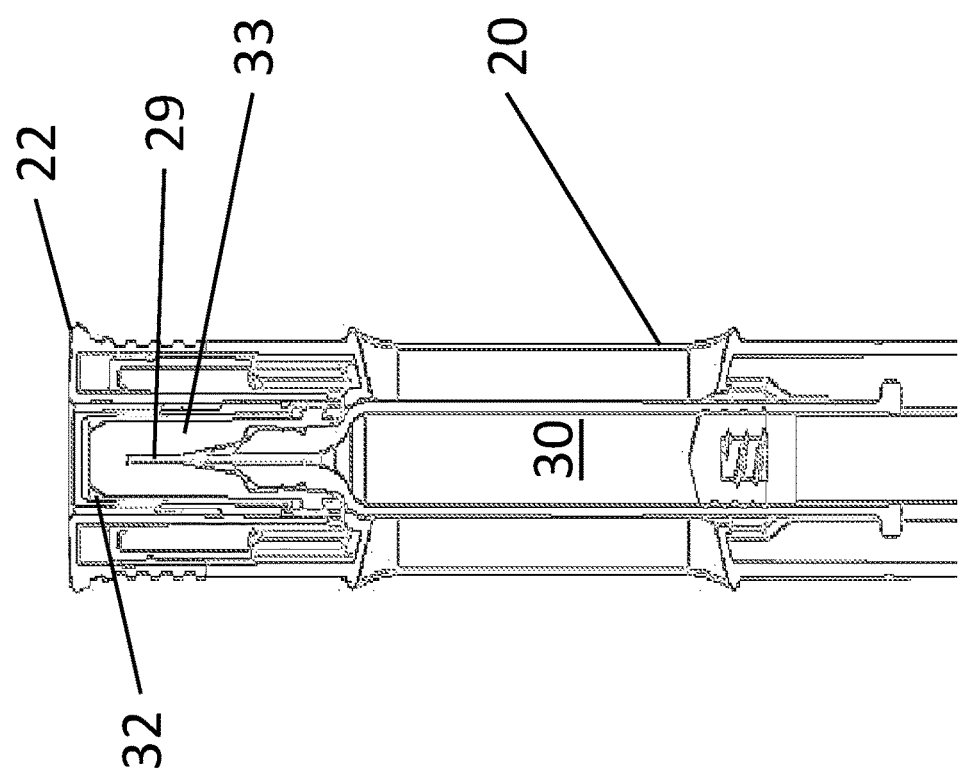
FIG. 4 illustrates a further enlarged longitudinal sectional view of the proximal part of the medicament delivery device.

FIG. 4 shows a proximal part of the medicament delivery device, more particularly, the proximal tubular housing 20, the cap 22 and a medicament container 30. The medicament container 30 comprises a movable stopper 35. The medicament container 30 is coaxially arranged and supported within the proximal tubular housing 20. The medicament container 30 is supported in the proximal tubular housing in such a manner that it is prevented from being movable in relation to the proximal tubular housing 20. The medicament container may also be arranged in a container holder (not shown) that is fixedly arranged within the proximal tubular housing 20. As shown in FIG. 4, the medicament container 30 is a syringe but it may also be a cartridge or the like. The syringe comprises a medicament delivery member 29 that is protected by the cap 22. More particularly, the medicament deliver member 29 is a needle or cannula when the medicament delivery device is an injector, but the medicament delivery member may also be a nozzle when the medicament delivery device is a nasal or eye spray delivery device. The medicament delivery member 29 may be protected by a sterile protecting member. When the medicament delivery member 29 is a needle, the sterile protecting member is a flexible needle shield 33 that may also be protected by a rigid needle shield 32.

Figure 5:
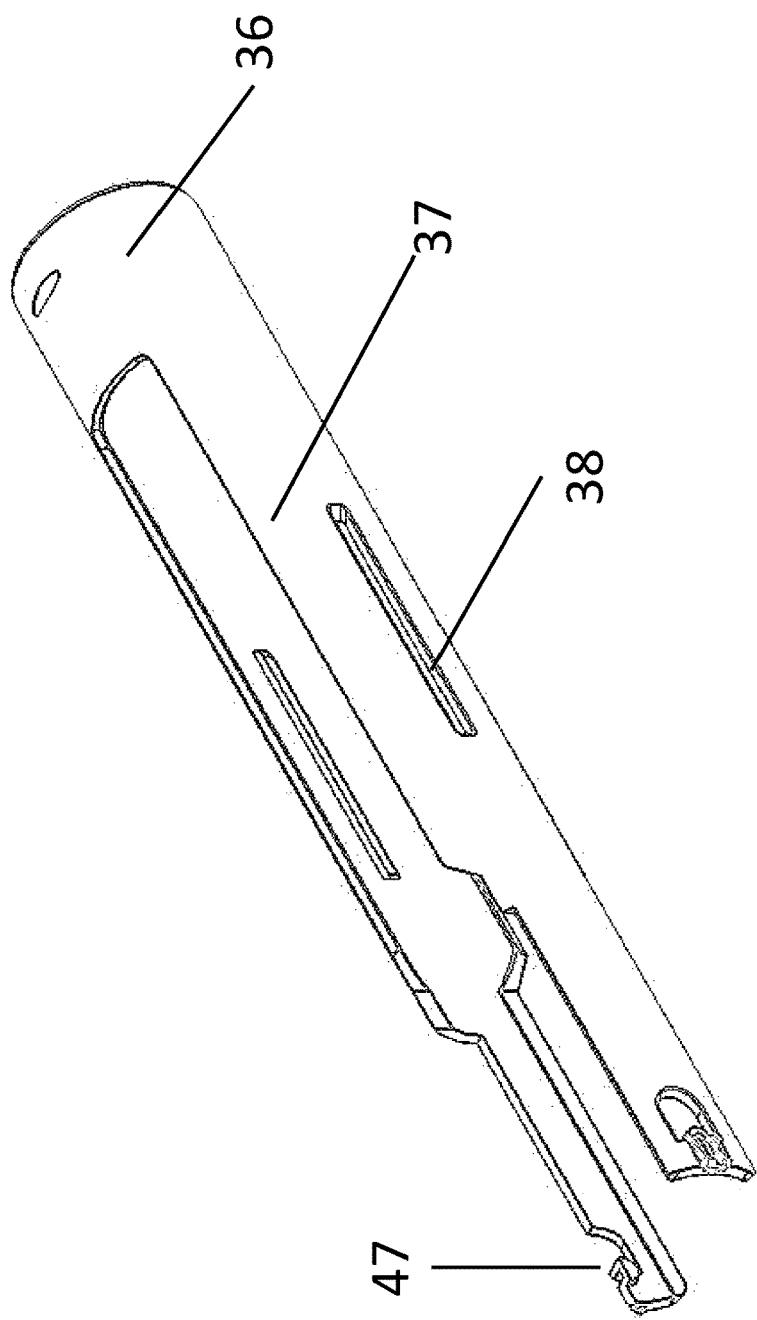
FIG. 5 depicts an enlarged perspective view illustrating details of a medicament delivery member cover.

FIG. 5 shows a medicament delivery member cover 31 which is comprised in the medicament delivery device. The medicament delivery member cover 31 has a tubular shape comprising a tubular proximal part 36 and two opposite cut outs whereby two distally extending tongues 37 are formed. Each distally extending tongue 37 comprises a longitudinally extending groove 38. At the distal end, each distally extending tongue 37 comprises a radially inwardly extending protrusion 47. The medicament delivery member cover 31 is biased and slidably arranged within the proximal tubular housing 20 wherein the longitudinally extending grooves 38 are configured to interact with corresponding longitudinally extending ribs (not shown) on the inner surface of the proximal tubular housing 20 for guiding and limiting the displacement of the medicament delivery member cover 31 in relation to the proximal tubular housing 20. The tubular proximal part 36 is forced to protrude proximally from the proximal tubular housing 20 by a resilient member (not shown) which is arranged between the proximal tubular housing 20 and the medicament delivery member cover 31. The resilient member may be a compression spring. The cap 22 is removably connected to the tubular proximal part 36 (not shown), preferably connected by friction but other types of attaching or connecting means can be used as positive and non-positive connecting means. The cap 22 may be arranged with means for removing the sterile protecting member when the front cap is removed from the tubular proximal part 36 of the medicament delivery member cover 31.

According to present disclosure, a drive mechanism for a medicament delivery device comprises a compression member 3 which comprising a first cavity containing a first volume fluid, and a second cavity containing a second volume of fluid; a passage for fluid communication between the first cavity and the second cavity; a first movable piston 4 arranged to seal the first cavity; a second movable piston 34 arranged to seal the second cavity; wherein a movement of the first movable piston 4 or of the second movable piston 34, by an applied force, causes a relative change of volume between the first volume of fluid and the second volume of fluid, via a fluid flow through said passage such that the respective second movable piston 34 or the first movable piston 4 is also moved. Further, the first movable piston 4 is longitudinally movable between a first position and a second position relative to the compression member 3 and the second movable piston 34 is movable between a third and a fourth position relative to the compression member 3. When the first movable piston is in the first position and the second movable piston is in the third position, the first volume of fluid is larger than the second volume of fluid. The fluid is preferably air.

The applied force between the movable piston and the second movable piston respectively can be a manual force, a force from an energy accumulating device or a propulsive force. According to a preferred embodiment, the drive mechanism further comprises a force member 11 configured to exert the applied force on the first movable piston 4. Thus, the drive mechanism also comprises an activator member 40 configured to releasably hold said first movable piston 4 in the first position when said first movable piston 4 is under the bias of said force member 11, such that the first movable piston is released by a displacement of the activator member 40 in relation to first movable piston. The drive mechanism further comprises the distal tubular housing 21 in which the compression member 3 is coaxially arranged and rotationally locked, and the connector member 8 connected to the proximal end of the distal tubular housing 21 for preventing a longitudinal and proximal displacement of the compression member 3. In a preferred embodiment, the second movable piston 34 is a plunger rod.

Figure 6:
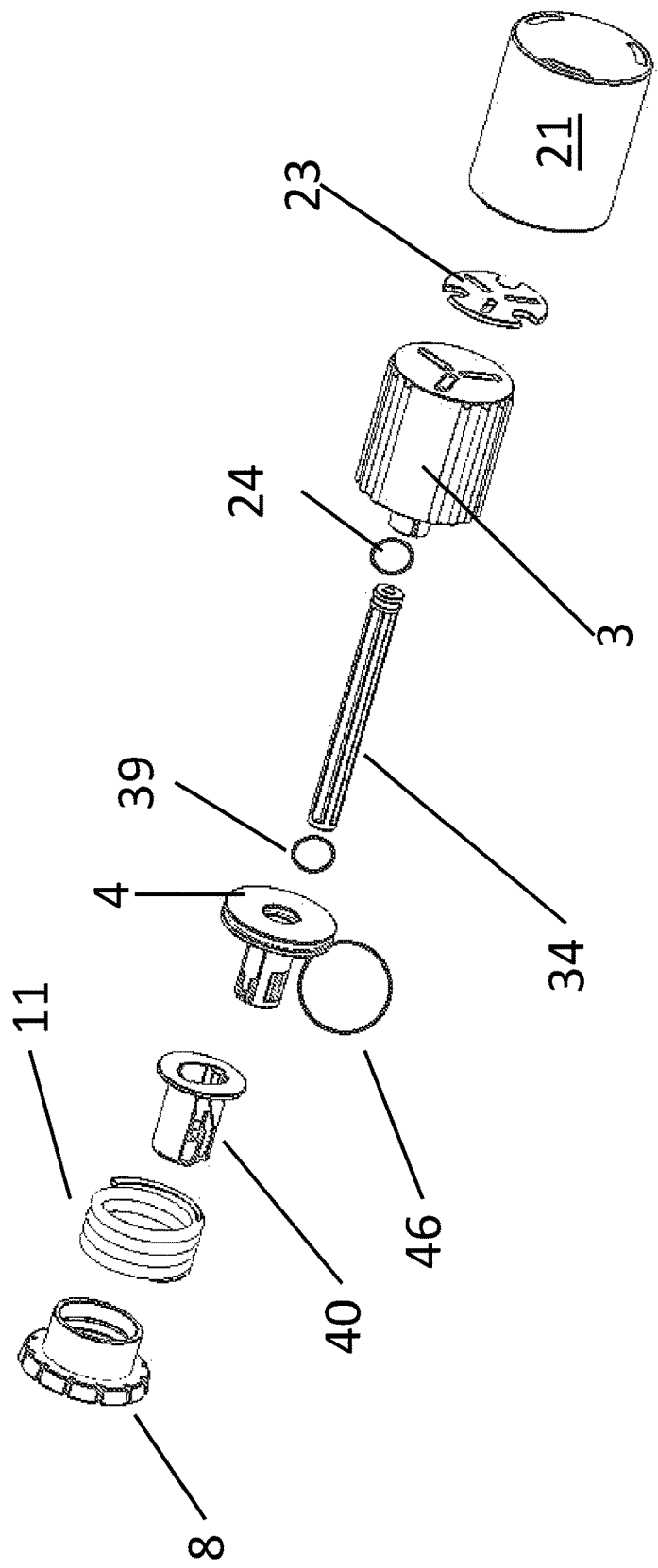
FIG. 6 shows an enlarged and exploded fragmented perspective view illustrating the components of the drive mechanism and its order in a preferred embodiment of the disclosure.

FIG. 6 shows the internal fragmented main parts of the drive mechanism according to a preferred embodiment. It is shown, the distal tubular housing 21; the compression member 3; the first movable piston 4; the force member 11; the activator member 40; and the connector member 8. FIG. 6 also shows a first seal 23 configured to be positioned between the distal tubular housing 21 and the compression member 3; a second seal 46, a third seal 39, and a fourth seal 24 for sealing the cavities and the passage in the preferred embodiment as will be explained below. In an alternative embodiment, the sealing of the passage is not necessary. The second, third and fourth seals are O-rings.

Figure 12:
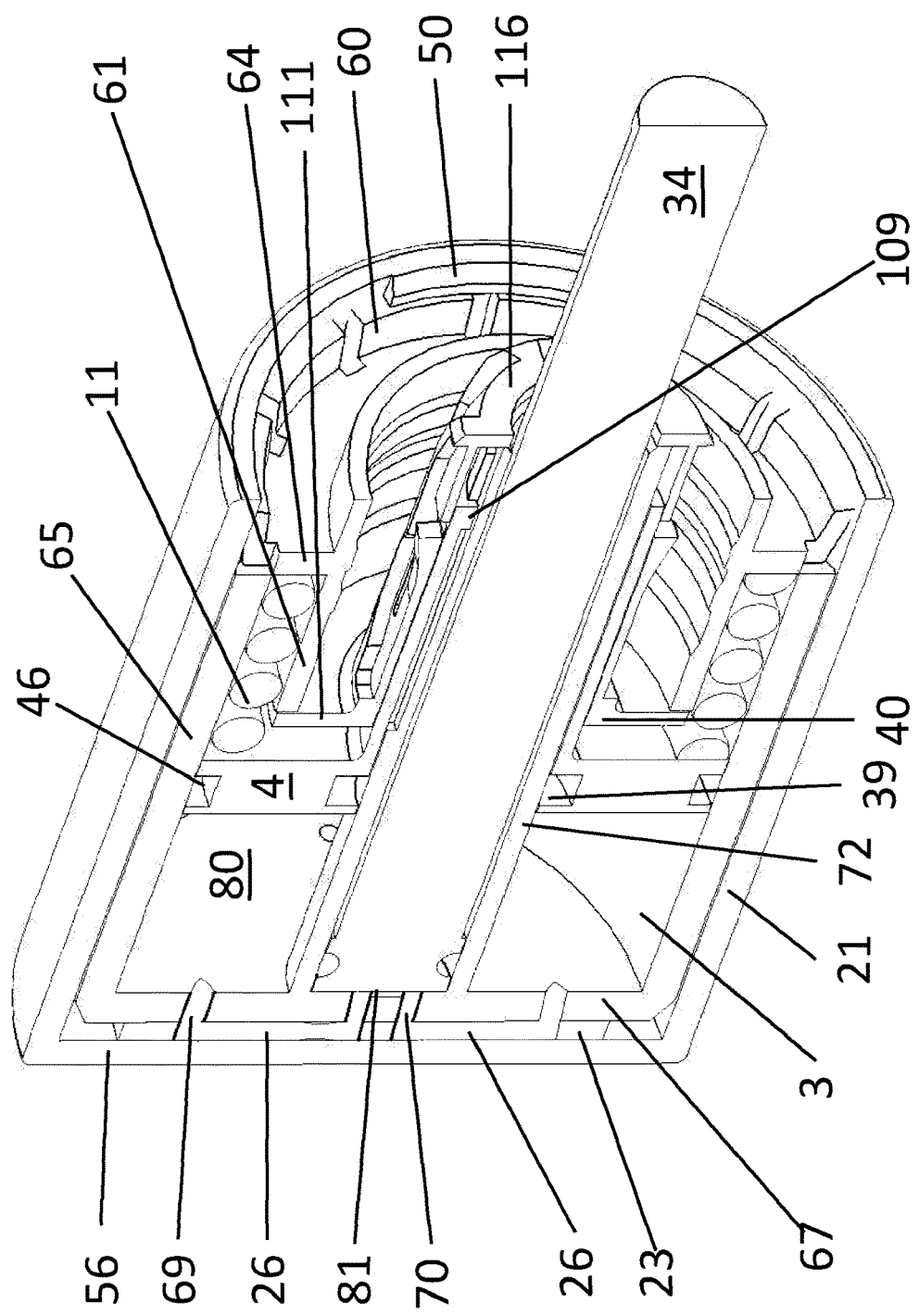
FIG. 12 illustrates an enlarged longitudinal sectional and perspective view of the drive mechanism when the first movable piston is in the first position.

In the preferred embodiment, as seen in FIG. 12, the equidistant resilient tongues 60 of the connector member 8 are configured to interact with the radially inwardly extending ledges 50 of the distal tubular housing 21 (see also FIG. 2). Also shown is the second movable piston 34. The second movable piston 34 comprises at its distal end an annular groove 130 configured to receive the fourth seal 24.

Figure 7:
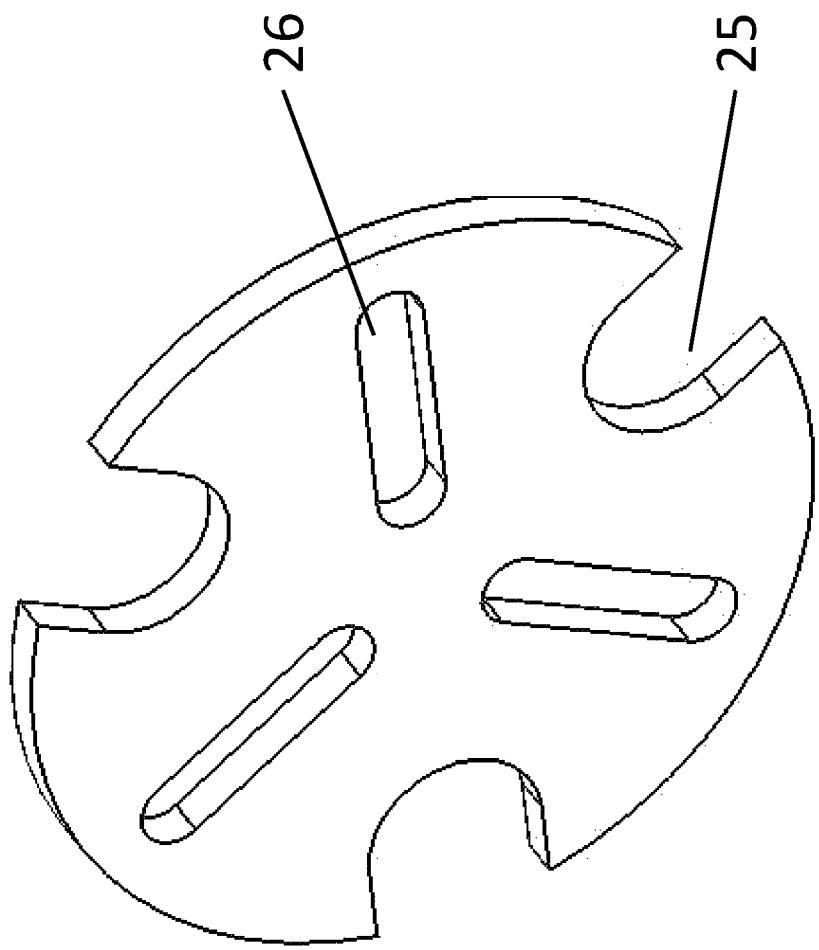
FIG. 7 shows a perspective view of a first seal with its openings and cut-outs.

FIG. 7 shows the first seal 23, which is a gasket. The first seal 23 is disk shaped and comprises equidistant cut-outs 25 configured to fit with the equidistant proximally extending protrusions 52 of the distal tubular housing 21, FIG. 3. Equidistant elongated openings 26 of the first seal 23 are configured to fit the equidistant elongated depressions 52, FIG. 3, of the distal tubular housing 21. The equidistant cut-outs 25 and the equidistant elongated openings 26 are alternately arranged in relation to each other. In the preferred embodiment, the equidistant elongated openings 26 and the equidistant elongated depressions 52 are formed having an elliptical or oval shape.

Figure 8:
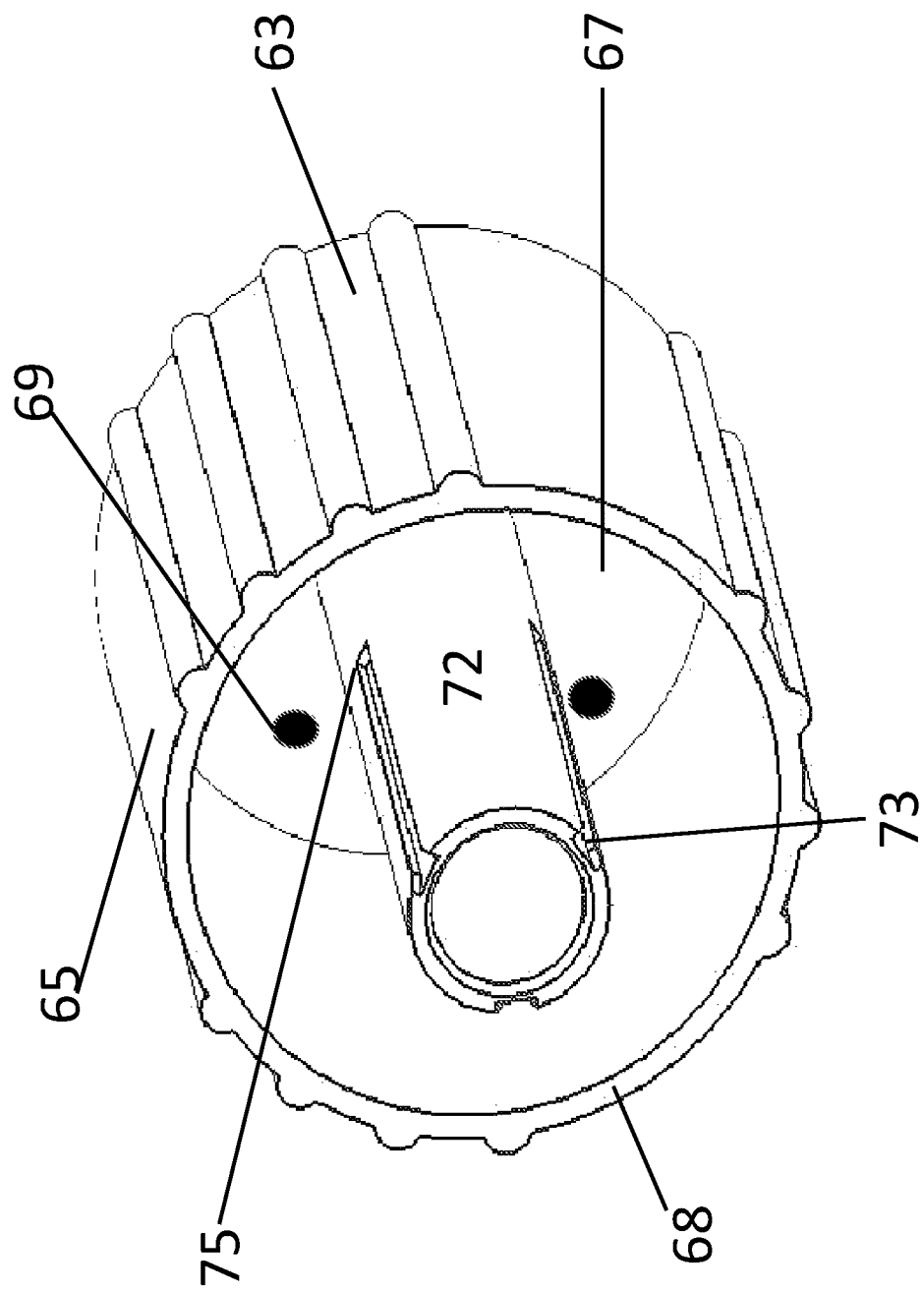
FIG. 8 illustrates an enlarged perspective view of a compression member.

FIG. 8 shows the compression member 3, which comprises a transversal distal plate 67 having an outer tubular sleeve 65 and an inner tubular sleeve 72 coaxially arranged with each other and extending proximally from the distal plate 67. The compression member 3 is configured to be positioned within the distal tubular housing 21. The outer tubular sleeve 65 comprises on its outer surface longitudinally extending tracks 63 configured to interact with the longitudinal extending ribs 55 of the distal tubular housing 21 for preventing any rotational movement of the compression member 3 in relation to the distal tubular housing 21 i.e. the compression member 3 is longitudinally and rotationally locked to the distal tubular housing. The distal plate 67 is integrated with the outer tubular sleeve 65 at its distal end. The inner tubular sleeve 72 protrudes from the distal plate 67 in a longitudinally extending proximal direction. The inner tubular sleeve 72 comprises on its outer surface longitudinally extending grooves 73 which extend distally from the proximal rim of the inner tubular sleeve 72, a predetermined distance ending in a heel 75. Further, the longitudinal section of the inner tubular sleeve 72 is longer than the longitudinal section of the outer tubular sleeve 65, such that it protrudes a predetermined distance proximally of the outer tubular sleeve 65. The space between the inner surface of the outer tubular sleeve 65, a part of the distal plate 67 and the outer surface of the inner tubular sleeve 72 defines the first cavity 80. The tubular space surrounded by the inner surface of the inner tubular sleeve 72 and a part of the transversal distal plate 67 defines the second cavity 81.

Figure 9:
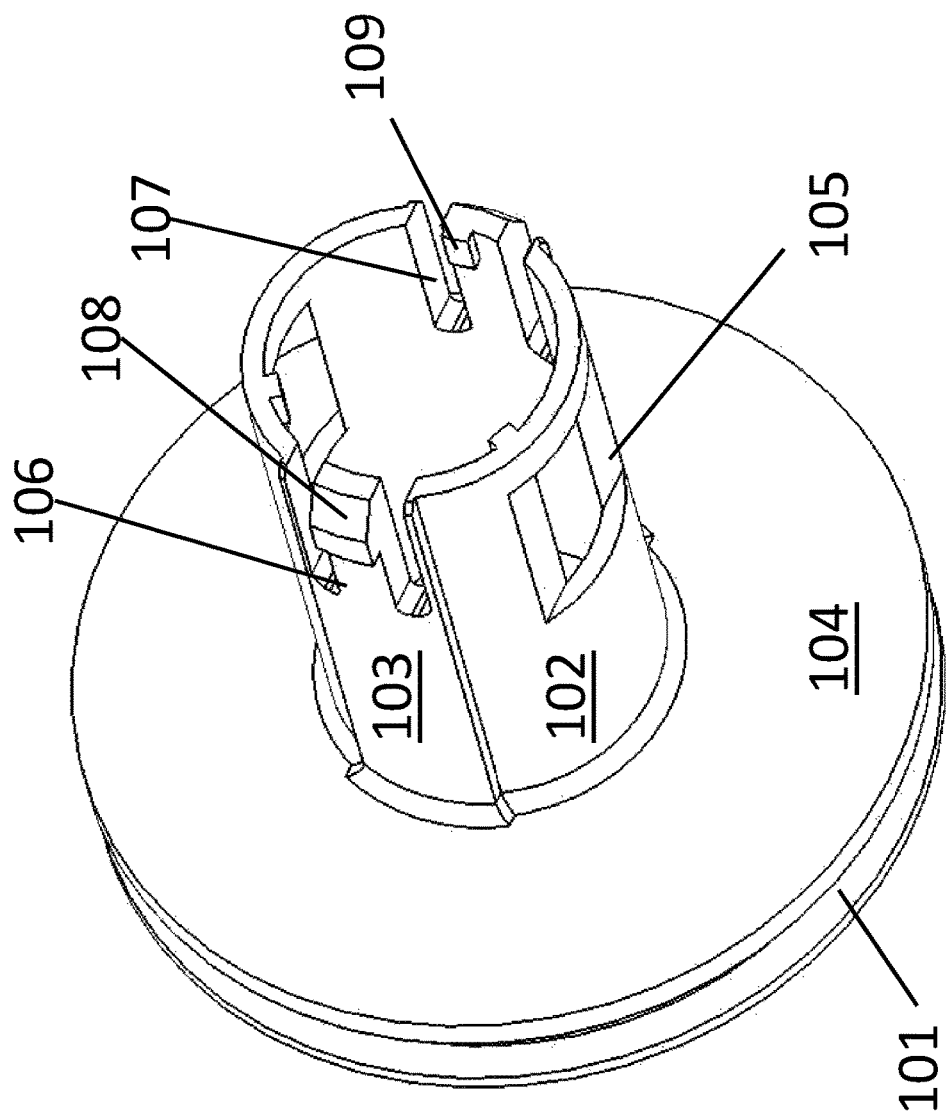
FIG. 9 shows a perspective view of a first movable piston.

FIG. 9 shows the first movable piston 4 comprising a piston plate 104 and a piston sleeve 102. The piston plate 104 is washer-shaped and has an inner and outer rim. On its outer rim is formed a first annular groove 101 configured to receive the second seal 46 and on its inner rim is formed a second annular groove configured to receive the third seal 39 (as shown in FIG. 6). The piston sleeve 102 extends in a longitudinal proximal direction from the piston plate 104. On the outer surface of the piston sleeve 102 are formed two equidistant elevations 103 wherein two longitudinally extending cut-outs 107 are taken at the proximal part of the piston sleeve 102 forming a resilient tongue 106. At the proximal end of each resilient tongue 106 are formed a radial outwardly extending protrusion 108 and a radial inwardly extending protrusion 109. On the outer surface of the piston sleeve 102, two opposite windows 105 are formed.

Figure 10:
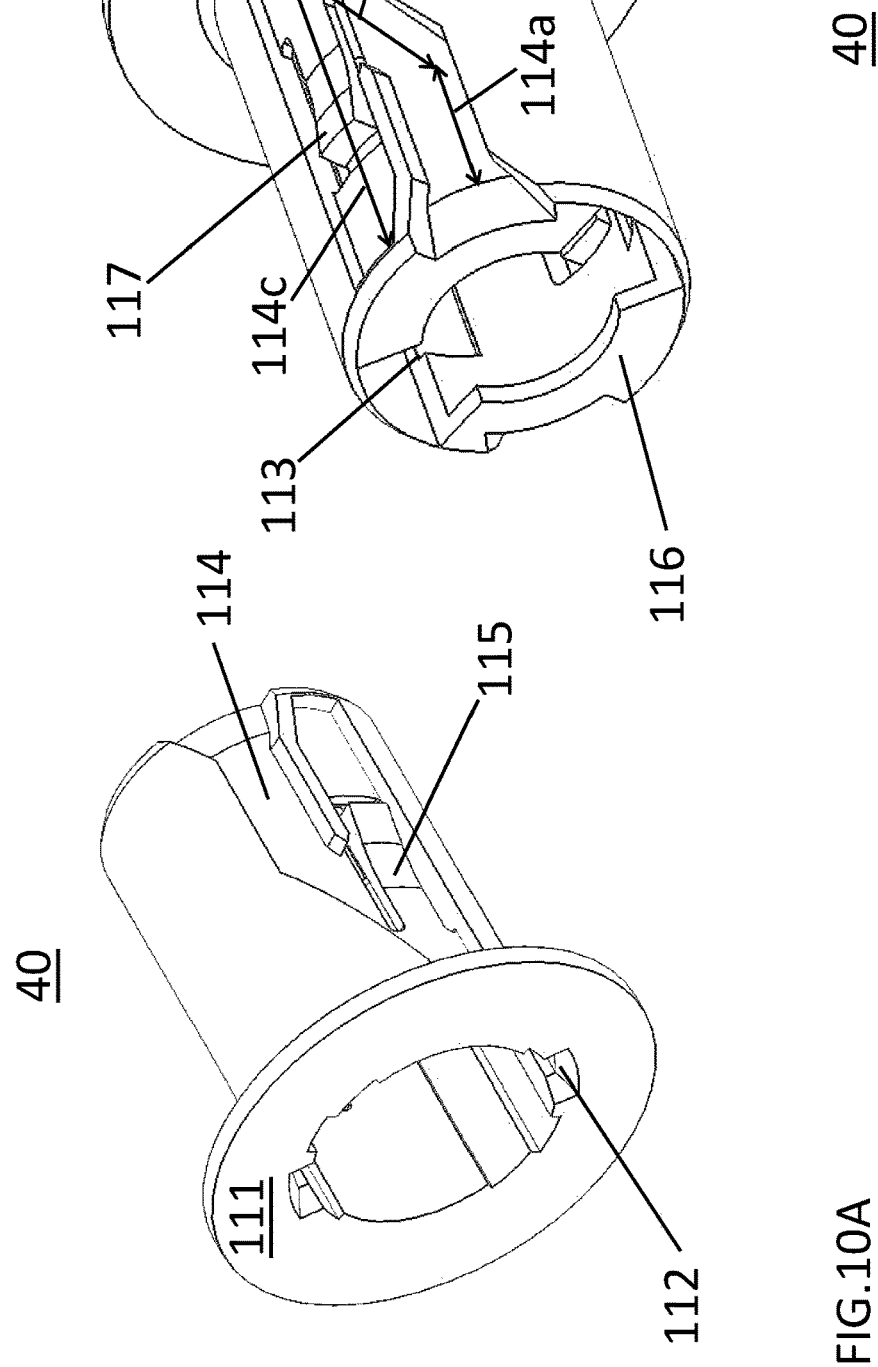
FIG. 10A-FIG. 10B shows a rear respectively a front enlarged perspective views of an activator member.

FIG. 10A-FIG. 10B respectively show the rear and the front enlarged perspective views of the activator member 40 which is tubularly shaped and configured to be positioned coaxially on the piston sleeve 102 and movable in relation to the first movable piston 4, more particularly rotatable and prevented to be slidable in relation to the first movable piston 4 (see also FIG. 12). The activator member 40 comprises an activator plate 111 which is washer-shaped, and an activator sleeve 110 extending proximally from the activator plate 111. On the inner surface of the activator sleeve 110, longitudinally extending tracks 112 are formed, configured to guide the equidistant elevations 103 of the piston sleeve 102 when the activator member 40 rotates in relation to the first movable piston 4. On the outer surface of the activator sleeve 110 are formed two equidistant guide tracks 114. Each guide track 114 comprises a cut-out forming a proximally extending resilient tongue 115 which has a wedge shaped protrusion 117 at its proximal end. Starting from the proximal rim of the activator sleeve 110, each guide track 114 comprises a first longitudinally extending track 114a, a second inclined and longitudinally extending track 114b and a third longitudinally extending track 114c, wherein the resilient tongue 115 is comprised in the third track. At the proximal rim of the activator sleeve two radially inwardly equidistant ledges 116 are formed for abutting the proximally-facing rim of the inner tubular sleeve 72 of the compression member 3, FIG. 12. The activator member 80 is prevented to be slidable towards the proximal end by the interaction between the proximally facing surface of the activator plate 111 and the distal end of the inner tubular sleeve 61.

Figure 11:
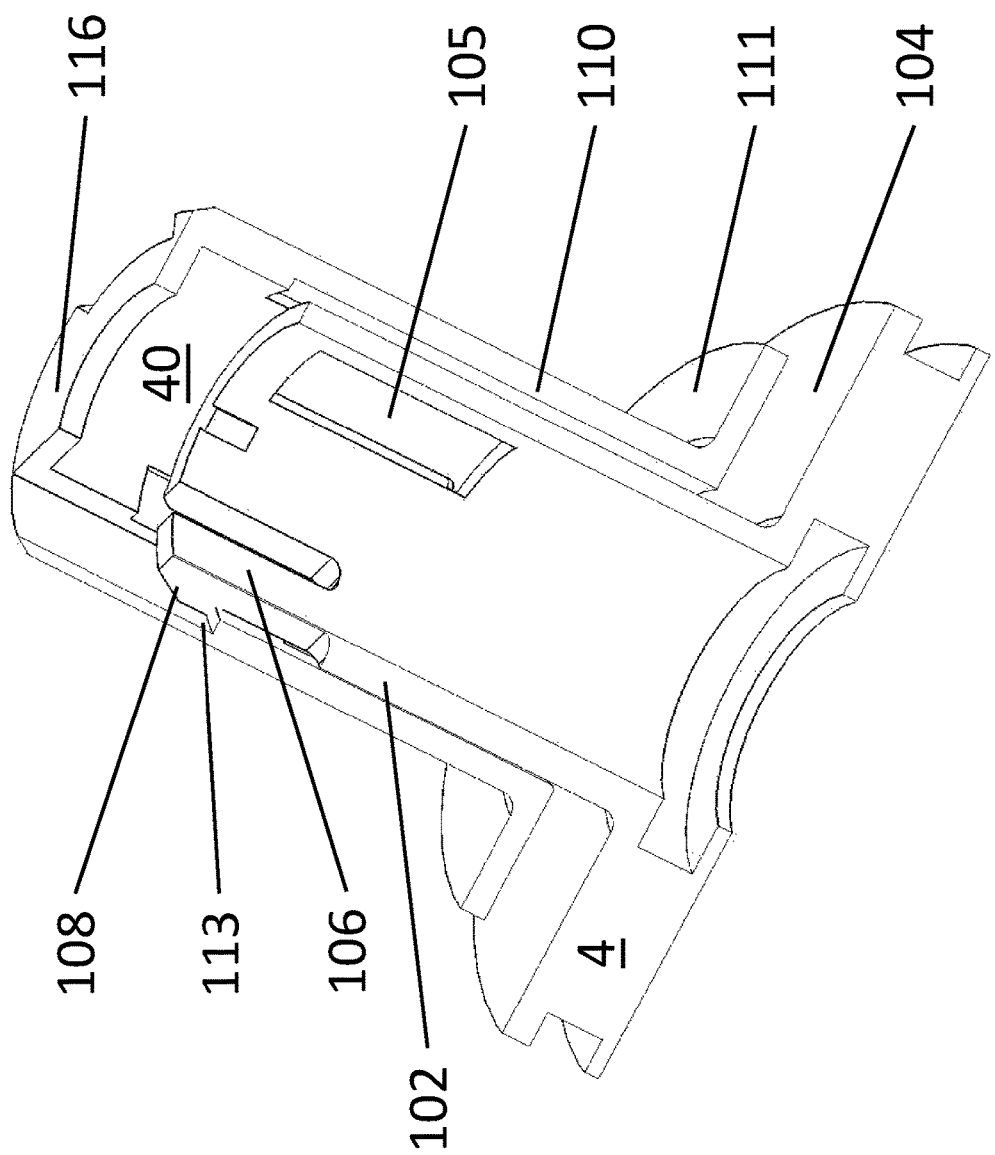
FIG. 11 shows a transverse sectional view of the first movable piston connected to the activator member when the first movable piston is in a first position.

Further, a cross-sectional, perspective view of the first movable piston 4 connected to the activator member 40 is depicted in FIG. 11. On the inner surface of the activator sleeve 110 are also formed radially inwardly extending ledges 113 configured to interact with the radially outwardly extending protrusions 108 on the resilient tongues 106 of the piston sleeve 102.

The passage is defined by a first part comprising a through-hole 69 on the distal plate 67 wherein said through-hole 69 communicates to the first cavity, a second part comprising a channel between the compression member 3 and the distal tubular housing 21 sealed by the first seal 23, and a third part comprising a through-hole 70 on the distal plate 67 wherein said through-hole 70 communicates to the second cavity. The channel between the compression member 3 and the distal tubular housing 21 sealed by the first seal 23 communicates the through holes 69 and 70.

In the preferred embodiment, as shown in FIG. 12, the first part comprises three through-holes 69, the second part comprises three channels and the third part comprises three through-holes 70. Each channel is defined by equidistant elongated depression 51 of the distal tubular housing 21, the inner boundary of a equidistant elongated opening 26 of the first seal 23 and the surface of on the distal plate 67 which is surrounded by the boundary of the equidistant elongated opening 26 of the first seal 23.

In an alternative embodiment (not shown), the passage is defined by a first part comprising a through-hole 69 on the outer tubular sleeve 65 of the compression member 3, a second part comprising a channel between the compression member 3 and the distal tubular housing 21 sealed by the first seal 23, and a third part comprising a through-hole 70 on the distal plate 67 wherein said through hole 70 communicates with the second cavity.

In a further alternative embodiment (not shown), the passage is defined by a through-hole located at the distal end of the inner tubular sleeve 72.

FIG. 12 shows an enlarged longitudinal cross-sectional and perspective view of the drive mechanism in the preferred embodiment. In the shown figure, the drive mechanism is assembled. The first seal 23 is arranged within tubular distal housing 21 abutting the distal transversal wall 56 of the distal tubular housing 21. The equidistant cut-outs 25 of the first seal 23 are arranged to align with the equidistant proximally extending protrusions 52 on the distal plate 67 of the compression member 3 and the inner boundary of each equidistant elongated opening 26 of the first seal 23 is arranged to align with the corresponding boundary of each equidistant elongated depression 51 of the distal tubular housing 21 such that the channel of the passage is formed. The compression member 3 is coaxially arranged within the distal tubular housing 21 and its distal plate 67 is abutting the first seal 23. The longitudinally extending tracks 63 of the compression member 3 interact with the longitudinal extending ribs 55 of the distal tubular housing 21 for preventing a relative rotational movement.

Further, the first movable piston 4 is, more specifically, longitudinally slidable in relation to the compression member 3. The second seal 46 is abutting the inner surface of the outer tubular sleeve 65 and the third seal 39 is abutting the outer surface of the inner tubular sleeve 72. As shown in FIG. 12, the radially inwardly extending protrusions 109 of the first movable piston 4 are arranged in the longitudinally extending grooves 73 on the inner tubular sleeve 72 of the compression member 3 such that when the first movable piston 4 slides longitudinally in relation to the compression member 3, a relative rotational movement is prevented. The first movable piston 4 is arranged such that it is movable i.e. longitudinally slidable, from the first position wherein the radially inwardly extending protrusions 109 of the first movable piston 4 are positioned closest to the proximal rim of the inner tubular sleeve 72 to the second position wherein the radially inwardly extending protrusions 109 of the first movable piston 4 are positioned abutting the heel 75 of the longitudinally extending grooves 73 on the inner tubular sleeve 72 of the compression member 3 (not shown). The activator member 40 is coaxially arranged on the piston sleeve 102 such that the radially inwardly equidistant ledges 116 abut the proximally-facing rim of the inner tubular sleeve 72 of the compression member 3.

FIG. 11. shows a transverse sectional view of the first movable piston connected to the activator member when the first movable piston is in the first position. The first movable piston 4 is releasably connected to the activator member 40 by the interaction between the radially outwardly extending protrusion 108 of the first movable piston and the radially inwardly extending ledges 113 of the activator member. When the activator member 40 is rotated in relation to the first movable piston 4, the radially outwardly extending protrusion 108 of the first movable piston 4 is released from the radially inwardly extending ledges 113 of the activator member 40

Further, FIG. 12 illustrates the connector member 8 coaxially arranged within the distal tubular housing 21 such that the equidistant resilient tongues 60 of the connector member 8 interact with the radially inwardly extending ledges 50 such that the compression member 3 and the activator member are prevented of moving towards the proximal end. Further, the distal end of the inner tubular sleeve 61 of the connector member 8 abuts the activator plate 111 of the activator member 40. The force member 11, e.g. a compression spring, is arranged between the radially outwardly extending ledge 64 of the connector member 8 and the piston plate 104 of the first movable piston 4. When the first movable piston 4 is in the first position, the force member 11 is in a compressed state. The second movable piston 34 is coaxially arranged, and longitudinally movable, within the second cavity 81 such that the fourth seal 24 is abutting the inner surface of the inner tubular sleeve 72. When the first movable piston 4 is in the first position, the first volume of fluid is in the first cavity, and the second movable piston is in the third position wherein the second volume of fluid is in the second cavity. The first volume of fluid is larger than the second volume of fluid when the first movable piston is in the first position and the second movable piston is in the third position. Thus, the distal end of the second movable piston 34 is nearer the distal plate 67 of the compression member 3 than the piston plate 104 of the first movable piston 4.

Figure 13:
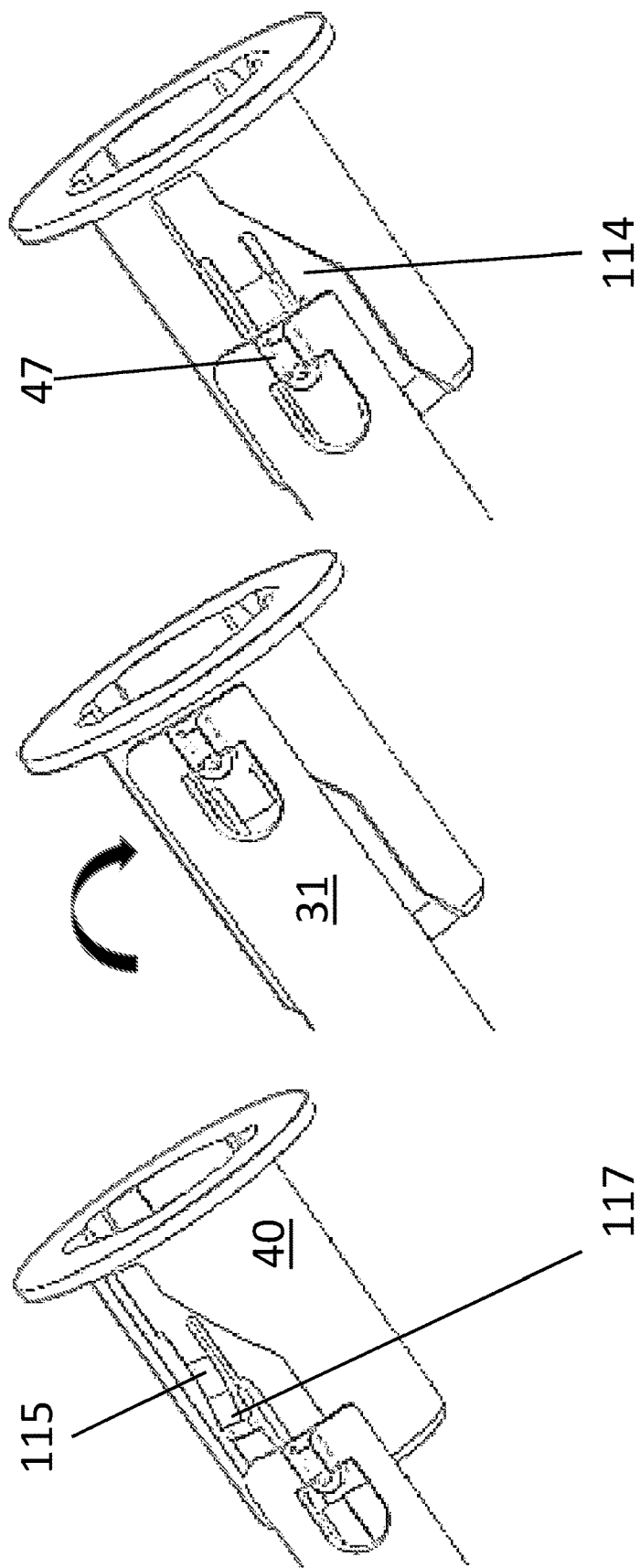
FIG. 13 shows three enlarged perspective views of the activator member rotational movement in relation to the medicament delivery member cover.

As seen in FIG. 13, the radially inwardly extending protrusions 47 of the medicament delivery member cover 31 are arranged in the guide tracks 114 of the activator member 40 such that when the medicament delivery member cover 31 is distally moved in relation to the activator member 40 against a bias of the resilient member which is arranged between the proximal tubular housing 20 and the medicament delivery member cover 31, the radially inwardly extending protrusions 47 initially interact with the first track 114a, followed by the second track 114b, forcing the activator member 40 to rotate in relation to the first movable piston 4. When the activator member is rotated, the proximally extending resilient tongues 115 of the activator sleeve 110 are aligned with the windows 105 of the piston sleeve. Further, when the medicament delivery member cover 31 is forced proximally by the bias of the resilient member, the radially inwardly extending protrusions 47 interact with the third track 114c wherein the radially inwardly extending protrusions 47 passes over the proximally extending resilient tongues 115, after which the proximal extending resilient tongues 115 flex back and the wedge shaped protrusion 117 of the proximal extending resilient tongue 115 interacts with the radially inwardly extending protrusions 47 whereby the medicament delivery member cover 31 is movably locked, more particularly the delivery member cover is prevented to be distally displaced when the user attempts to press it again against a delivery site.

When the activator member 40 is rotated, the radially outwardly extending protrusion 108 of the first movable piston 4 is released from the radially inwardly extending ledges 113 of the activator member 40 and since the force member 11 is in a compressed state, the first movable piston is forced to move distally from the first to the second position i.e. the first movable piston 4 is longitudinally slidable in relation to the compression member from the first position wherein the radially inwardly extending protrusions 109 of the first movable piston 4 are positioned closest to the proximal rim of the inner tubular sleeve 72 to the second position wherein the radially inwardly extending protrusions 109 of the first movable piston 4 are positioned abutting the heel 75 of the longitudinally extending grooves 73 on the inner tubular sleeve 72 of the compression member 3 (not shown).

Figure 14:
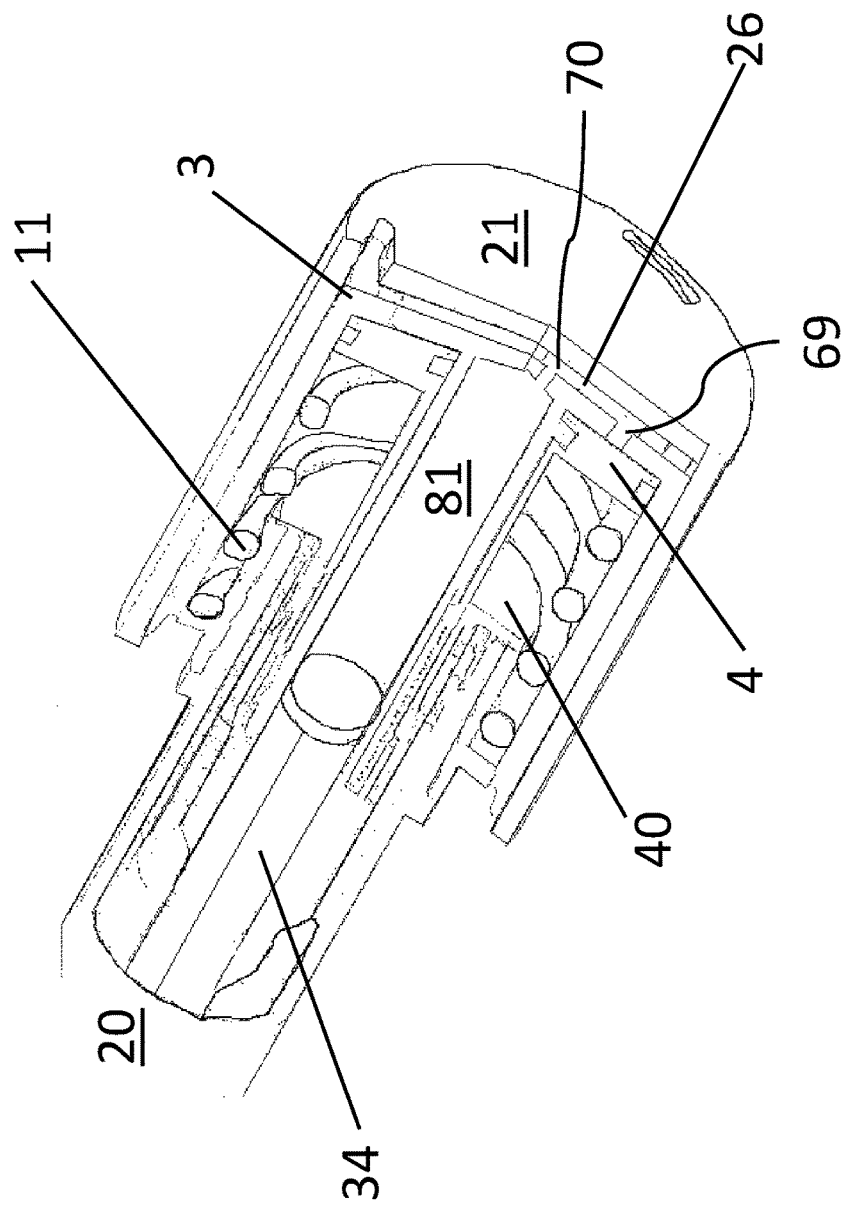
FIG. 14 shows an enlarged longitudinal sectional and perspective view of the drive mechanism when the first movable piston is in a second position.

FIG. 14 shows an enlarged cross-sectional and perspective view of the drive mechanism of the preferred embodiment. When the first movable piston 4 is forced from the first to the second position, said movement causes a relative change of volume between the first volume of fluid and the second volume of fluid, via a fluid flow through the passage, such that the second movable piston is also moved from the third to the fourth position in which the distal end of the second movable piston 34 is furthest from the distal plate 67 of the compression member 3. Thus, most of the first volume of fluid in the first cavity is forced to flow through the passage whereby the second movable piston 34 is forced to move towards the proximal end. Then, the second volume of fluid is larger than the first volume of fluid when the first movable piston is in the second position and the second movable piston is in the fourth position. Since the proximal end of the second movable piston 34 is abutting the movable stopper 35 of the medicament container, the movable stopper 35 is also forced to be moved towards the proximal end whereby the medicament is expelled through the medicament delivery member 29 (see also FIG. 12).

The drive mechanism may be a reloadable drive mechanism (not shown) such that after said drive mechanism has been used in a medicament delivery device to expel a predetermined dose of medicament, the medicament container can be exchanged. Thus, before connecting the proximal housing, in which the medicament container is positioned, to the distal housing; the drive mechanism is reloaded by forcing the second movable piston 34 to be moved from the fourth to the third position such that said movement causes a relative change of volume between the second volume of fluid and the first volume of fluid, via a fluid flow through the passage, whereby the first movable piston is also moved from the second to the first position. Thus, most of the second volume of fluid in the second cavity is forced to flow through the passage whereby the first movable piston is forced to move towards the proximal end. Then, again the first volume of fluid is larger than the second volume of fluid. The, first movable piston interacts with the activator member such that the first movable piston becomes releasably connected to the activator member again.

The medicament delivery device may for example be an injector, a nasal or an eye dispenser or an inhaler. The inventive concept has mainly been described above with reference to a few examples. However, as is readily appreciated by a person skilled in the art, other embodiments than the ones disclosed above are equally possible within the scope of the inventive concept, as defined by the appended claims. For example the passages which are first and second through-holes located on the distal plate may also be located at the distal end of the inner tubular sleeve, more particularly on the distal periphery of the inner tubular sleeve.

The invention claimed is:

1. A drive mechanism for a medicament delivery device comprising:
    a compression member axially and rotationally fixed within a first housing of the medicament delivery device, where the compression member comprises a first cavity containing a first volume of fluid, said compression member also comprising a second cavity containing a second volume of fluid, and where the compression member is prevented from proximal and distal longitudinal displacement relative to the first housing during all use of the drive mechanism by a connector fixedly attached to a proximal end of the first housing, where the connector comprises an inner connector configured to allow attachment of a second housing containing a medicament container, where inner connector prevents any relevant movement between the first housing and the second housing;
    a passage for fluid communication between the first cavity and the second cavity;
    a first movable piston arranged to seal the first cavity and to move in the distal direction relative to the compression member when the drive mechanism is activated to expel medicament from the medicament container; and
    a second movable piston arranged within an inner tubular sleeve to seal the second cavity and to move in the proximal direction relative to the compression member simultaneously with the first movable piston moving in the distal direction such that a proximal end of the second movable piston acts directly on the medicament container to expel the medicament from the medicament container;
    wherein axial movement of the first movable piston or of the second movable piston relative to the compression member, by an applied force, causes a relative change of volume between the first volume of fluid and the second volume of fluid, via a fluid flow through said passage, such that the respective second movable piston or the first movable piston is also moved.

2. The drive mechanism according to claim 1, wherein the first movable piston is longitudinally movable between a first position and a second position relative to the compression member and wherein the second movable piston is movable between a third and a fourth position relative to the compression member.

3. The drive mechanism according to claim 2, wherein the first volume of fluid is larger than the second volume of fluid when the first movable piston is in the first position and the second movable piston is in the third position.

4. The drive mechanism according to claim 1, wherein the drive mechanism further comprises a force member configured to exert the force on the first movable piston.

5. The drive mechanism according to claim 4, wherein the drive mechanism further comprises an activator member configured to releasably hold said first movable piston in the first position when said first movable piston is under a bias of said force member.

6. The drive mechanism according to claim 5, wherein the first movable piston is released by a displacement of the activator member in relation to the first movable piston.

7. The drive mechanism according to claim 4, wherein the force member is arranged between the connector member and the first movable piston.

8. The drive mechanism according to claim 1, wherein the compression member comprises a distal plate having an outer tubular sleeve arranged coaxially with the inner tubular sleeve and wherein the first cavity is defined by a space between an inner surface of the outer tubular sleeve, the distal plate and an outer surface of the inner tubular sleeve, and wherein the second cavity is defined by the inner surface of the inner tubular sleeve and the distal plate.

9. The drive mechanism according to claim 8, wherein the passage is defined by a through-hole located at a distal end of the inner tubular sleeve.

10. The drive mechanism according to claim 8, wherein the drive mechanism further comprises a first seal which is positioned between the first housing and the compression member creating a sealed space between the first housing and the compression member, which space is sealed from ambient pressure.

11. The drive mechanism according to claim 10, wherein the passage is defined by a first part comprising a first through-hole in the distal plate wherein said through-hole communicates with the first cavity, a second part comprising a channel between the compression member and the first housing through the space sealed by the first seal, and a third part comprising a second through-hole on the distal plate wherein said second through-hole communicates with the second cavity such that the channel between the compression member and the first housing sealed by the first seal communicates through both the first and second through-holes.

12. The drive mechanism according to claim 11, wherein the first seal comprises the second part of the channel.

13. The drive mechanism according to claim 10, wherein the first seal is a gasket.

14. A medicament delivery device comprising a drive mechanism according to claim 1.

15. A drive mechanism for a medicament delivery device comprising
- a compression member axially and rotationally fixed within a first housing of the medicament delivery device, where the compression member comprises a first cavity containing a first volume of fluid, said compression member also comprising a second cavity containing a second volume of fluid, and where a connector prevents the compression member from moving distally and proximally relative to the first housing during use of the of the drive mechanism to expel medicament from a container of medicament, where the connector is fixedly attached to a proximal end of the first housing comprises an inner connector configured to allow attachment of a second housing containing the medicament container;
- a passage for fluid communication between the first cavity and the second cavity;
- a first movable piston arranged to seal the first cavity and to move in the distal direction relative to the compression member when the drive mechanism is activated to expel medicament from the medicament container; and
- a second movable piston arranged to seal the second cavity and to move in the proximal direction relative to the compression member when the first movable piston moves in the distal direction;
- wherein movement of the first movable piston or of the second movable piston, by an applied force, causes a relative change of volume between the first volume of fluid and the second volume of fluid, via a fluid flow through said passage, such that the respective second movable piston or the first movable piston is also moved,
- wherein the first movable piston is longitudinally movable between a first position and a second position relative to the compression member, and wherein the second movable piston is movable between a third and a fourth position relative to the compression member, such that a proximal end of the second movable piston acts directly on the medicament container to expel the medicament from the medicament container.

16. The drive mechanism according to claim 15, wherein the drive mechanism further comprises a force member configured to exert the force on the first movable piston.

17. The drive mechanism according to claim 16, wherein the drive mechanism further comprises an activator member configured to releasably hold said first movable piston in the first position when said first movable piston is under a bias of said force member.

18. The drive mechanism according to claim 16, wherein the force member is arranged between the connector member and the first movable piston.

* * * * *